(12) United States Patent
Lemonis

(10) Patent No.: US 10,869,780 B2
(45) Date of Patent: Dec. 22, 2020

(54) OPTIMIZATION OF SPHERICAL ABERRATION PARAMETERS FOR CORNEAL LASER TREATMENT

(71) Applicant: Novartis AG, Basel (CH)

(72) Inventor: Sissimos Lemonis, Schwaig (DE)

(73) Assignee: Alcon Inc.

( * ) Notice: Subject to any disclaimer, the term of this patent is extended or adjusted under 35 U.S.C. 154(b) by 0 days.

(21) Appl. No.: 15/735,724

(22) PCT Filed: Feb. 10, 2017

(86) PCT No.: PCT/IB2017/050764
§ 371 (c)(1),
(2) Date: Dec. 12, 2017

(87) PCT Pub. No.: WO2018/146520
PCT Pub. Date: Aug. 16, 2018

(65) Prior Publication Data
US 2020/0022838 A1    Jan. 23, 2020

(51) Int. Cl.
*A61F 9/008* (2006.01)
*A61B 3/11* (2006.01)

(52) U.S. Cl.
CPC .......... *A61F 9/008* (2013.01); *A61F 9/00808* (2013.01); *A61B 3/112* (2013.01); *A61F 2009/00872* (2013.01); *A61F 2009/00878* (2013.01); *A61F 2009/00895* (2013.01)

(58) Field of Classification Search
CPC .. A61F 9/008; A61F 9/00802; A61F 9/00804; A61F 9/00808; A61F 2009/00861; A61F 2009/00872; A61F 2009/00878; A61F 2009/00895
See application file for complete search history.

(56) References Cited

U.S. PATENT DOCUMENTS

2003/0199858 A1* 10/2003 Schelonka .............. A61F 9/008
606/5
2008/0195086 A1    8/2008 Schroeder et al.
2013/0324983 A1   12/2013 Liang

FOREIGN PATENT DOCUMENTS

DE         102006003549         7/2007

* cited by examiner

*Primary Examiner* — Eugene T Wu
(74) *Attorney, Agent, or Firm* — Kenneth D. Bassinger, Esq.

(57) ABSTRACT

A method for determining spherical aberration parameters for a corneal laser treatment to treat presbyopia may include performing pupillometry to measure various actual pupil diameters of a patient from a photopic diameter to a mesopic diameter. An actual pupil center of the patient may also be measured. The measured pupil diameters and the pupil center may be used to customize the spherical aberration parameters to the eye of the patient for improved ocular results after treatment.

14 Claims, 4 Drawing Sheets

400 — METHOD FOR OPTIMIZING SPHERICAL ABERRATION PARAMETERS

402 PERFORM PUPILLOMETRY ON A PATIENT SUBJECT TO A CORNEAL LASER TREATMENT TO DETERMINE RESPECTIVE PUPIL DIAMETERS INCLUDING: A MESOPIC DIAMETER, A NORMAL LIGHT DIAMETER, AN ACCOMMODATIVE READING DIAMETER, AND A PHOTOPIC DIAMETER

404 PERFORM THE PUPILLOMETRY TO MEASURE A PUPIL CENTER OF THE PUPIL

406 CALCULATE AN OUTER DIAMETER FOR THE SPHERICAL ABERRATION THAT IS GREATER THAN THE MESOPIC DIAMETER

408 CALCULATE AN INNER DIAMETER ASSOCIATED WITH AN AMPLITUDE OF THE SPHERICAL ABERRATION THAT CORRESPONDS TO THE PHOTOPIC DIAMETER

410 CALCULATE THE AMPLITUDE OF THE SPHERICAL ABERRATION ACCORDING TO A REFRACTION THAT INDUCES MYOPIA

412 CALCULATE A SLOPE OF THE SPHERICAL ABERRATION EXTENDING FROM THE PHOTOPIC DIAMETER TO THE NORMAL LIGHT DIAMETER

414 CALCULATE A CENTER OF THE SPHERICAL ABERRATION BASED ON THE PUPIL CENTER

416 USING THE SPHERICAL ABERRATION CALCULATED, INCLUDING THE OUTER DIAMETER, THE INNER DIAMETER, THE AMPLITUDE, AND THE SLOPE, PERFORM THE CORNEAL LASER TREATMENT ON THE PATIENT

FIG. 4

OPTIMIZATION OF SPHERICAL ABERRATION PARAMETERS FOR CORNEAL LASER TREATMENT

BACKGROUND

Field of the Disclosure

The present disclosure relates to ophthalmic surgery, and more specifically, to optimization of spherical aberration parameters for corneal laser treatment.

Description of the Related Art

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). The diagnosis and specification of sphero-cylindrical spectacles and contact lenses for treatment of myopia, hyperopia, and astigmatism are well-established. Some surgery-based techniques, such as LASIK to reshape the cornea, are in wide-spread use and can yield good corrective results, but may not be as predictable as desired. In particular, LASIK for presbyopia may result in varying outcomes for different patients, which is undesirable.

SUMMARY

In one aspect, a disclosed method is for optimization of spherical aberration parameters for corneal laser treatments. The method may include performing pupillometry on a patient subject to a corneal laser treatment to measure respective pupil diameters including: a mesopic diameter, a normal light diameter, an accommodative reading diameter, and a photopic diameter. The method may also include calculating an outer diameter for the spherical aberration that is greater than the mesopic diameter, calculating an inner diameter for the spherical aberration associated with an amplitude of the spherical aberration that corresponds to the photopic diameter, calculating the amplitude of the spherical aberration according to a refraction that induces myopia, and calculating a slope of the spherical aberration extending from the photopic diameter to the normal light diameter. The method may further include using the spherical aberration calculated, including the outer diameter, the inner diameter, the amplitude, and the slope, performing the corneal laser treatment on the patient.

In any of the disclosed embodiments of the method, performing the pupillometry may further include determining a pupil center of the pupil, while the method may further include calculating a center of the spherical aberration based on the pupil center.

In any of the disclosed embodiments of the method, the corneal laser treatment may be a presbyopia treatment.

In any of the disclosed embodiments of the method, the corneal laser treatment may be performed using a laser-assisted in situ keratomileusis (LASIK).

In any of the disclosed embodiments of the method, calculating the slope of the spherical aberrations may include adding higher-order spherical aberrations.

In a further aspect, a laser parameter system for optimization of spherical aberration parameters for corneal laser treatments is disclosed. The laser parameter system may include a processor having access to memory media storing instructions executable by the processor. In the laser parameter system, the instructions may be executable by the processor to receive pupillometry data for a patient subject to a corneal laser treatment, the pupillometry data comprising respective pupil diameters including: a mesopic diameter, a normal light diameter, an accommodative reading diameter, and a photopic diameter. The instructions may further be executable to calculate an outer diameter for the spherical aberration that is greater than the mesopic diameter, calculate an inner diameter for the spherical aberration associated with an amplitude of the spherical aberration that corresponds to the photopic diameter, calculate the amplitude of the spherical aberration according to a refraction that induces myopia, and calculate a slope of the spherical aberration extending from the photopic diameter to the normal light diameter. Using the spherical aberration calculated, including the outer diameter, the inner diameter, the amplitude, and the slope, the instructions may be executable to cause the corneal laser treatment to be performed on the patient.

In any of the disclosed embodiments of the laser parameter system, the pupillometry data may further include a pupil center of the pupil, while the instructions may further be executable to calculate a center of the spherical aberration based on the pupil center.

In any of the disclosed embodiments of the laser parameter system, the corneal laser treatment may be a presbyopia treatment.

In any of the disclosed embodiments of the laser parameter system, the corneal laser treatment may be performed using a laser-assisted in situ keratomileusis (LASIK).

In any of the disclosed embodiments of the laser parameter system, the instructions to calculate the slope of the spherical aberrations may include instructions to add higher-order spherical aberrations.

Other disclosed aspects include an optical measurement instrument, such as an optical measurement instrument for performing pupillometry. In another aspect, the optical measurement instrument may be integrated within a laser system for performing corneal laser treatments, such as a LASIK system. The laser parameter system may be integrated with the optical measurement instrument, the laser system, or both.

BRIEF DESCRIPTION OF THE DRAWINGS

For a more complete understanding of the present invention and its features and advantages, reference is now made to the following description, taken in conjunction with the accompanying drawings, in which:

FIG. 4 is a flow chart of selected elements of a method for optimizing spherical aberration parameters for corneal laser treatment.

DESCRIPTION OF PARTICULAR EMBODIMENT(S)

Figure 1:
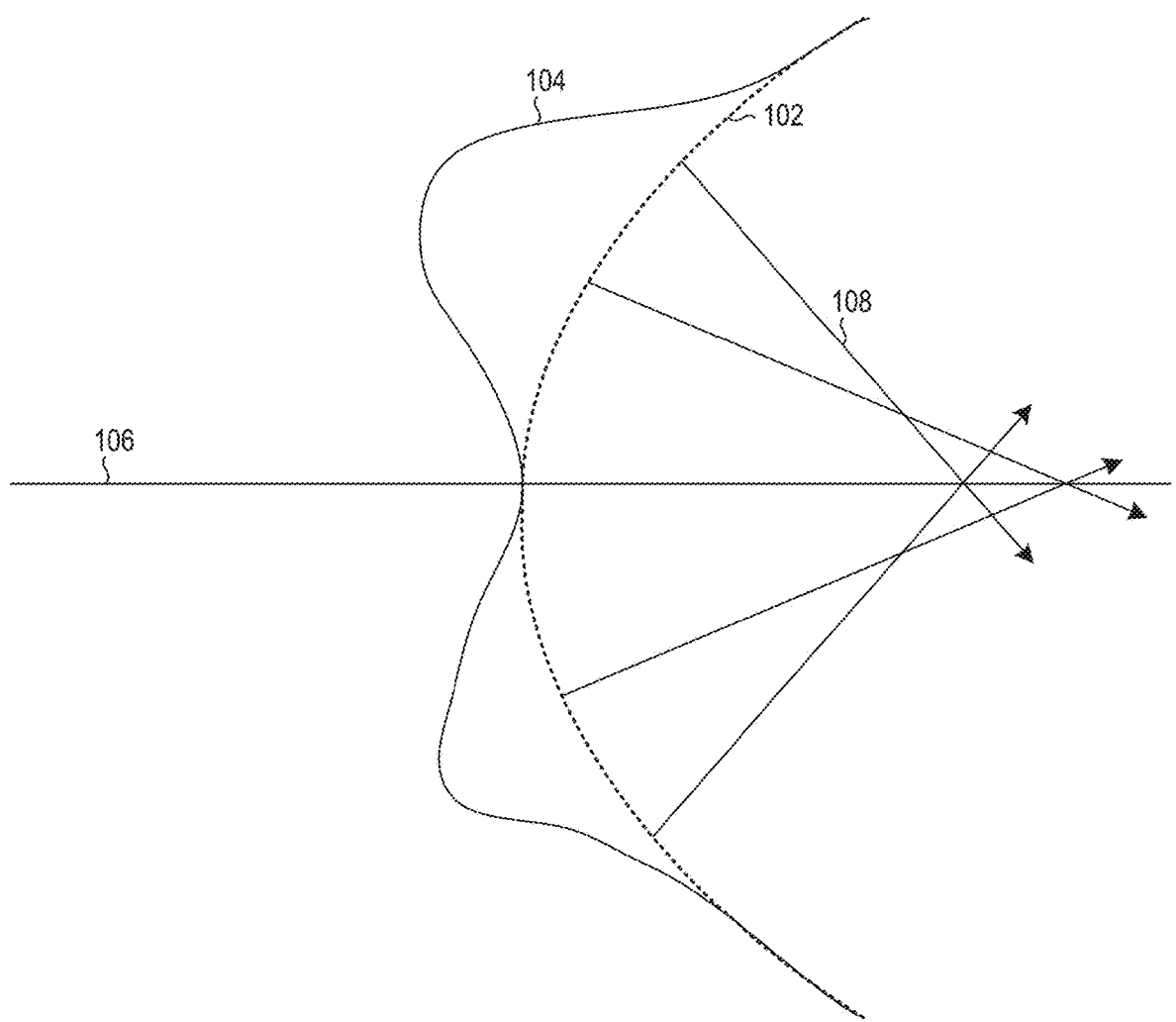
FIG. 1 is a depiction of spherical aberration of the cornea.

In the following description, details are set forth by way of example to facilitate discussion of the disclosed subject matter. It should be apparent to a person of ordinary skill in the field, however, that the disclosed embodiments are exemplary and not exhaustive of all possible embodiments.

Throughout this disclosure, a hyphenated form of a reference numeral refers to a specific instance of an element and the un-hyphenated form of the reference numeral refers to the element generically or collectively. Thus, as an example (not shown in the drawings), device "12-1" refers to an instance of a device class, which may be referred to collectively as devices "12" and any one of which may be referred to generically as a device "12". In the figures and the description, like numerals are intended to represent like elements.

As noted above, various ophthalmological techniques have been developed to correct ocular aberrations to improve the vision of patients. More recently, LASIK has been used to correct presbyopia by generating refraction using a spherical aberration of the cornea. The spherical aberration to correct presbyopia may result in a refractive myopia, particularly when the eye is adjusted for reading, in which an accommodation reflex includes myosis or constriction of the pupil to a photopic state. For all other pupil sizes, the eye should be in emmetropia, and in particular, the dominant eye should be exactly as emmetropic as possible.

Furthermore, it is well known that different individuals have different pupil parameters, such as photopic diameter, mesopic diameter, as well as eccentricity of the pupil center from the corneal center, the iris center, or the visual axis of the eye. However, current methods of calculating spherical aberration of the cornea to correct for presbyopia do not consider the biometric variations of the size and eccentricity of the pupil under various lighting conditions. As a result, the outcomes of LASIK to perform spherical aberration of the cornea may result in reduced refractive target realization, varying degrees of visual acuity (both for near and far vision), as well as certain undesired visual side-effects, such as starbursts, halos, among others.

As will be described in further detail, the inventor of the present disclosure has developed a method for optimization of spherical aberration parameters for corneal laser treatment that aligns the amplitude, slope, and diameter of the applied spherical aberration with the actual physical dimensions of the patient's pupil. The method for optimization of spherical aberration parameters for corneal laser treatment disclosed herein may accordingly improve presbyopia laser treatment, such as LASIK, by improving visual acuity outcomes for patients. The method for optimization of spherical aberration parameters for corneal laser treatment disclosed herein may further reduce or eliminate undesired visual side-effects.

Referring now to the drawings, FIG. 1 illustrates a depiction of an embodiment of a spherical aberration of the cornea 100. FIG. 1 is a schematic diagram for descriptive purposes and is not drawn to scale or perspective. In spherical aberration of the cornea 100, an optical axis 106 represents an optical axis of a human eye, while reference profile 102 may represent a spherical surface. Furthermore, anterior corneal profile 104 may represent spherical aberrations at a surface of the cornea that are shown relative to reference profile 102. For example, when performing a corneal laser treatment, anterior corneal profile 104 may depict the resulting spherical aberrations of the cornea. Also shown in FIG. 1 are rays 108, which depict how light is expected to focus along various points falling on optical axis 106. For example, the points may be selected to correspond to a location of the retina under various optical conditions to facilitate visual acuity. In this manner, anterior corneal profile 104 may be formed to create variations in refraction of incoming rays (not shown) that will result in a desired visual acuity. Although anterior corneal profile 104 is shown as a cross-sectional profile, it will be understood that circular symmetry may be applied about optical axis 106 to represent anterior corneal profile 104 in three dimensions. It is noted that anterior corneal profile 104 may further include certain asymmetric features, in various embodiments.

As noted previously, spherical aberration parameters may be used to calculate anterior corneal profile 104. Then, based on the spherical aberration parameters, anterior corneal profile 104 may be created in the cornea using a laser treatment, such as LASIK. In this manner, various vision conditions may be treated and improved visual acuity may be obtained. For example, anterior corneal profile 104 may be used to treat presbyopia, which results from age-related decrease in accommodation of the lens (not shown).

Figure 2:
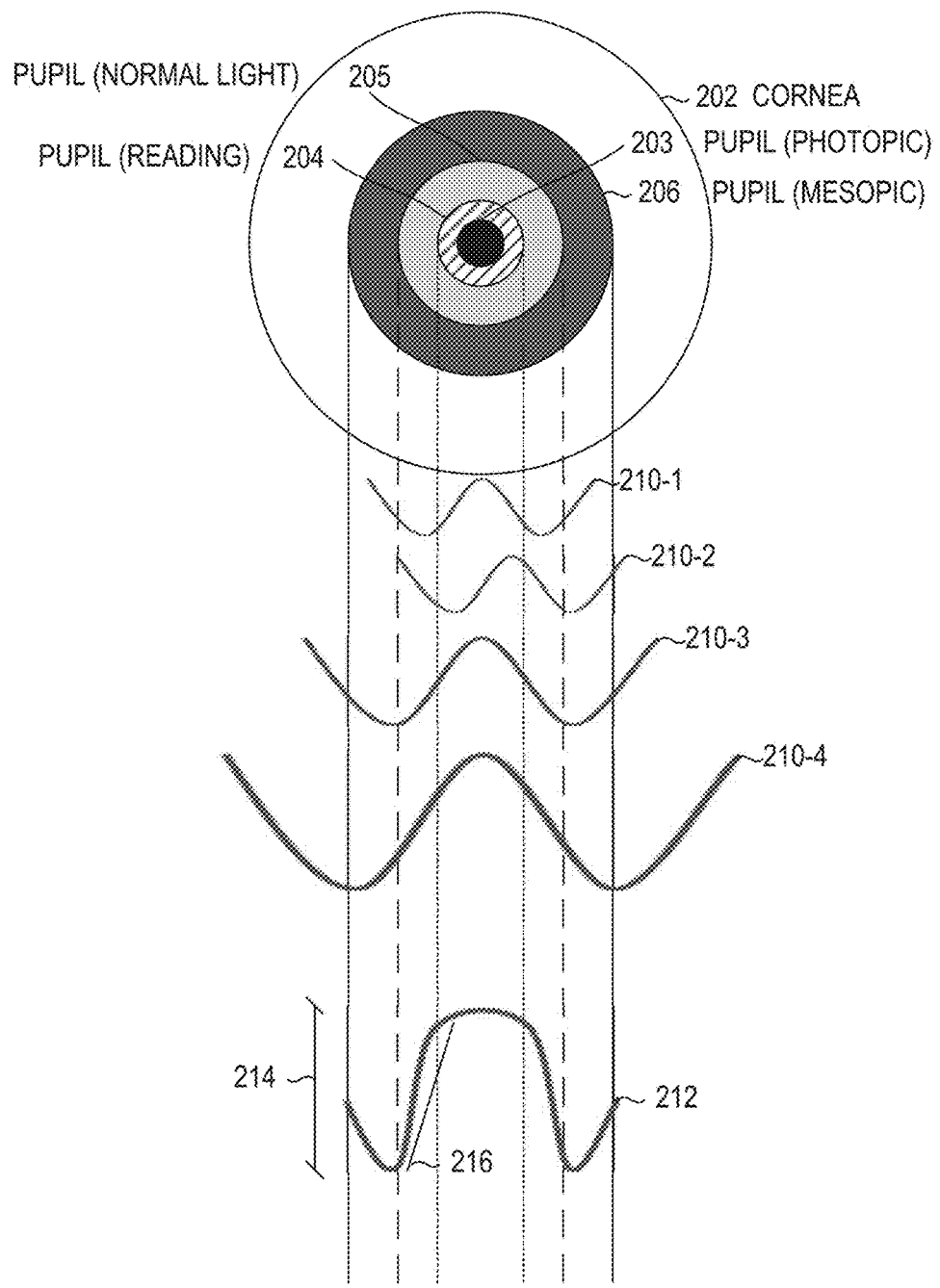
FIG. 2 is a depiction of cornea and pupil size with spherical aberration of the cornea.

Referring now to FIG. 2, a depiction of an embodiment of corneal and pupil size with spherical aberration 200 is illustrated. FIG. 2 is a schematic diagram for descriptive purposes and is not drawn to scale or perspective. At the top of FIG. 2 a depiction of a cornea 202 includes representations of pupils of varying diameters, including photopic pupil 203, an accommodative reading pupil 204, a normal light pupil 205, and a mesopic pupil 206, which are shown superimposed. At the bottom of FIG. 2, conventional spherical aberrations 210 and optimized spherical aberration 212 are shown as curves along an arbitrary horizontal axis corresponding to the pupil diameters. The amplitude of conventional spherical aberrations 210 and optimized spherical aberration 212 are also shown as an arbitrary scale and are intended to be similar to anterior corneal profile 102 shown in FIG. 1.

In FIG. 2, mesopic pupil 206 corresponds to a pupil diameter under low light conditions, such as moonlight, for example, while photopic pupil 203 corresponds to a pupil diameter under bright light conditions, such as outdoor sunlight, for example. Accordingly, normal light pupil 205 corresponds to a pupil diameter under indoor lighting conditions, such as in an office or in a working environment. Furthermore, accommodative reading pupil 204 corresponds to a pupil diameter during an accommodative reflex while reading at a relatively close distance. When a patient has presbyopia, the pupil may continue to narrow to accommodative reading pupil 204, but the lens (not shown) of the eye may no longer be able to focus while reading.

In FIG. 2, conventional spherical aberrations 210 illustrate various conditions when the spherical aberration of the eye that is applied during corneal laser treatment does not align with the actual diameters of the pupil. Typically, conventional spherical aberrations 210 are formed as shown, in a general form that is similar to a sine wave. Although conventional spherical aberrations 210 are shown having various sizes and positions, while cornea 202 including the various pupil diameters remains fixed in FIG. 2, it will be understood that conventional spherical aberrations 210 illustrate a relative mismatch to the various pupil diameters, representing the same mismatch when the pupil diameters vary from one patient to another patient.

In FIG. 2, conventional spherical aberration 210-1 does not extend to the diameter of mesopic pupil 206 and thus, some light outside of conventional spherical aberration 210-1 will enter the pupil. As a result, conventional spherical aberration 210-1 may cause undesired visual side-effects, such as starbursts, halos, among others. Further, conventional spherical aberration 210-2 is not centered about cornea 202 or any of the various pupil diameters shown, which may arise from eccentricity in the iris or the pupil that causes the pupil centroid to shift. Accordingly, conventional spherical aberration 210-2 may also cause undesired visual side-effects, such as starbursts, halos, among others. Next, conventional spherical aberration 210-3 is centered and does extend beyond the diameter of mesopic pupil 206. However, conventional spherical aberration 210-3 is not optimized in amplitude or slope to provide sufficient refraction over the area of accommodative reading pupil 204. As a result, conventional spherical aberration 210-3 is poorly suited to treat presbyopia effectively and may not lead to desirable clinical outcomes when applied, because only a small portion of the aberration is at an amplitude to create enough refraction to have myopia within accommodative reading pupil 204. Finally, conventional spherical aberration 210-4 is centered and does extend beyond the diameter of mesopic pupil 206, and does have more amplitude at the area corresponding to accommodative reading pupil 204. However, the slope of conventional spherical aberration 210-4 extends through mesopic pupil 206, and as a result, the refraction exhibited will be dependent upon the pupil diameter in a range that varies greatly during daytime light exposure. Thus, conventional spherical aberration 210-4 will result in widely varying visual acuity that may differ starkly from patient to patient, which is undesirable.

In FIG. 2, optimized spherical aberration 212 depicts a spherical aberration that has been optimized for the various pupil diameters depicted within cornea 202 to treat presbyopia. Specifically, optimized spherical aberration 212 extends in diameter just beyond the pupil diameter of mesopic pupil 206 and is centered on the pupil center. Furthermore, optimized spherical aberration 212 has an amplitude 214 that corresponds to a refraction for myopia over the entire pupil diameter of accommodative reading pupil 204, which is effective to negate presbyopia. Also, optimized spherical aberration 212 has a slope 216 that is optimized relative to the pupil diameters between normal light pupil 205 and photopic pupil 203. For example, slope 216 may be formed as a sharp drop-off by addition of additional higher order spherical aberrations to the calculation of optimized spherical aberration 212. Because optimized spherical aberration 212 is generated using actual measured values from the patient's eye, optimized spherical aberration 212 will result in more precise correction of presbyopia for different patients, and will be customized to provide each individual patient optimal results.

Figure 3:
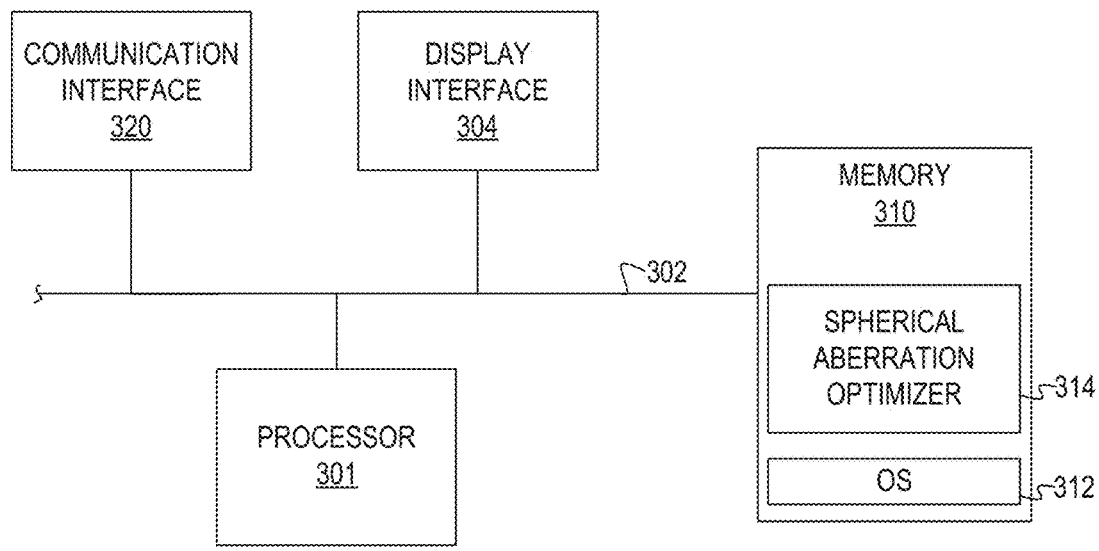
FIG. 3 is a block diagram of selected elements of a laser parameter system.

Referring now to FIG. 3, a block diagram illustrating selected elements of an embodiment of laser parameter system 300 is presented. Laser parameter system 300 may be enabled to perform optimization of spherical aberration parameters for corneal laser treatment, as disclosed herein. In certain embodiments, laser parameter system 300 may be integrated, or coupled to, a laser treatment system, such as a LASIK system. For example, laser parameter system 300 may be used to generate or apply optimized spherical aberration 212 to a laser treatment, as described herein.

In the embodiment depicted in FIG. 3, laser parameter system 300 includes processor 301 coupled via shared bus 302 to memory media collectively identified as memory 310. Laser parameter system 300, as depicted in FIG. 3, further includes communication interface 320 that can interface to various external entities, such as laser treatment systems, and pupillometry systems, among other devices. In some embodiments, communication interface 320 is operable to enable laser parameter system 300 to connect to a network (not shown in FIG. 3). In embodiments, as depicted in FIG. 3, laser parameter system 300 includes display interface 304 that connects shared bus 302, or another bus, with an output port for one or more displays.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a spherical aberration optimizer 314. Operating system 312 may be a UNIX or UNIX-like operating system, a Windows® family operating system, or another suitable operating system. Spherical aberration optimizer 314 may perform any of the various methods and calculations described herein.

Referring now to FIG. 4, a flow chart of selected elements of an embodiment of a method 400 for optimizing spherical aberration parameters for corneal laser treatment. It is noted that certain operations described in method 400 may be optional or may be rearranged in different embodiments. Method 400 may be performed using an optical measurement instrument (not shown), such as an optical measurement instrument for performing pupillometry. In certain embodiments, the optical measurement instrument may be integrated within a laser system for performing corneal laser treatments.

Method 400 may begin, at step 402, by performing pupillometry on a patient subject to a corneal laser treatment to determine respective pupil diameters including: a mesopic diameter, a normal light diameter, an accommodative reading diameter, and a photopic diameter. At step 404, the pupillometry is performed to measure a pupil center of the pupil. At step 406, an outer diameter for the spherical aberration is calculated that is greater than the mesopic diameter. At step 408, an inner diameter associated with an amplitude of the spherical aberration is calculated that corresponds to the photopic diameter. At step 410, the amplitude of the spherical aberration is calculated according to a refraction that induces myopia. At step 412, a slope of the spherical aberration is calculated extending from the photopic diameter to the normal light diameter. In some embodiments, calculating the slope of the spherical aberrations includes adding additional spherical aberrations. In step 412, a desired refractive target, corresponding to normal light pupil 205, may be aimed for, as well as a desired myopic induction for accommodative reading pupil 204. At step 414, a center of the spherical aberration is calculated based on the pupil center. At step 416, using the spherical aberration calculated, including the outer diameter, the inner diameter, the amplitude, and the slope, the corneal laser treatment is performed on the patient. The corneal laser treatment may be performed using a LASIK treatment. The corneal laser treatment may be applied to treat presbyopia, according to the methods described herein.

As disclosed herein, a method for determining spherical aberration parameters for a corneal laser treatment to treat presbyopia may include performing pupillometry to measure various actual pupil diameters of a patient from a photopic diameter to a mesopic diameter. An actual pupil center of the patient may also be measured. The measured pupil diameters and the pupil center may be used to customize the spherical aberration parameters to the eye of the patient for improved ocular results after treatment.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for optimization of spherical aberration parameters for corneal laser treatments, the method comprising:
    performing pupillometry on a patient subject to a corneal laser treatment to measure respective pupil diameters including: a mesopic diameter, a normal indoor light diameter, an accommodative reading diameter, and a photopic diameter;
    calculating an outer diameter for the spherical aberration that is greater than the mesopic diameter;
    calculating an inner diameter for the spherical aberration associated with an amplitude of the spherical aberration that corresponds to the photopic diameter;
    calculating the amplitude of the spherical aberration according to a refraction that induces myopia;
    calculating a slope of the spherical aberration extending from the photopic diameter to the normal indoor light diameter to provide optimized spherical aberration over a pupil area extending from the measured accommodative reading diameter to the measured photopic diameter; and
    using the spherical aberration calculated, including the outer diameter, the inner diameter, the amplitude, and the slope, performing the corneal laser treatment on the patient.

2. The method of claim 1 wherein the spherical aberration is myopic over a pupil area extending from the pupil center to the measured accommodative reading diameter.

3. The method of claim 2 wherein the spherical aberration is emmetropic over a pupil area extending from the measured accommodative reading diameter to the measured mesopic pupil diameter.

4. The method of claim 1, wherein performing the pupillometry further comprises determining a pupil center of the pupil, and further comprising:
    calculating a center of the spherical aberration based on the pupil center.

5. The method of claim 1, wherein the corneal laser treatment is a presbyopia treatment.

6. The method of claim 1, wherein the corneal laser treatment is performed using a laser-assisted in situ keratomileusis (LASIK).

7. The method of claim 1, wherein calculating the slope of the spherical aberrations includes adding higher-order spherical aberrations.

8. A laser parameter system for optimization of spherical aberration parameters for corneal laser treatments, the system comprising:
    a processor having access to memory media storing instructions executable by the processor to:
        receive pupillometry data for a patient subject to a corneal laser treatment, the pupillometry data comprising respective pupil diameters including: a mesopic diameter, a normal indoor light diameter, an accommodative reading diameter, and a photopic diameter;
        calculate an outer diameter for the spherical aberration that is greater than the mesopic diameter;
        calculate an inner diameter for the spherical aberration associated with an amplitude of the spherical aberration that corresponds to the photopic diameter;
        calculate the amplitude of the spherical aberration according to a refraction that induces myopia;
        calculate a slope of the spherical aberration extending from the photopic diameter to the normal indoor light diameter to provide optimized spherical aberration over a pupil area extending from the measured accommodative reading diameter to the measured photopic diameter; and
        using the spherical aberration calculated, including the outer diameter, the inner diameter, the amplitude, and the slope, cause the corneal laser treatment to be performed on the patient.

9. The laser parameter system of claim 8 wherein the spherical aberration is myopic over a pupil area extending from the pupil center to the measured accommodative reading diameter.

10. The laser parameter system of claim 9 wherein the spherical aberration is emmetropic over a pupil area extending from the measured accommodative reading diameter to the measured mesopic pupil diameter.

11. The laser parameter system of claim 8, wherein the pupillometry data further comprise a pupil center of the pupil, and wherein the instructions are further executable to:
    calculate a center of the spherical aberration based on the pupil center.

12. The laser parameter system of claim 8, wherein the corneal laser treatment is a presbyopia treatment.

13. The laser parameter system of claim 8, wherein the corneal laser treatment is performed using a laser-assisted in situ keratomileusis (LASIK).

14. The laser parameter system of claim 8, wherein the instructions to calculate the slope of the spherical aberrations include instructions to add higher-order spherical aberrations.

* * * * *